United States Patent
Kuwana et al.

(10) Patent No.: US 9,862,656 B2
(45) Date of Patent: Jan. 9, 2018

(54) METHOD FOR PRODUCING PARAFFINS (71) Applicant: Sumitomo Seika Chemicals Co., Ltd., Kako-Gun, Hyogo (JP)

(72) Inventors: Akihiro Kuwana, Hyogo (JP); Jun-ichi Sakamoto, Hyogo (JP); Hiroyuki Hata, Hyogo (JP)

(73) Assignee: SUMITOMO SEIKA CHEMICALS CO., LTD., Kako-Gun, Hyogo (JP)

( * ) Notice: Subject to any disclaimer, the term of this patent is extended or adjusted under 35 U.S.C. 154(b) by 169 days.

(21) Appl. No.: 14/364,734

(22) PCT Filed: Sep. 25, 2012

(86) PCT No.: PCT/JP2012/074561
§ 371 (c)(1),
(2) Date: Jun. 12, 2014

(87) PCT Pub. No.: WO2013/114667
PCT Pub. Date: Aug. 8, 2013

(65) Prior Publication Data
US 2014/0378721 A1 Dec. 25, 2014

(30) Foreign Application Priority Data

Feb. 3, 2012 (JP) .................................. 2012-022352

(51) Int. Cl.
*C07C 5/03* (2006.01)
*C07C 7/12* (2006.01)
(Continued)

(52) U.S. Cl.
CPC .................. *C07C 5/03* (2013.01); *C07C 5/08* (2013.01); *C07C 7/11* (2013.01); *C07C 7/12* (2013.01);
(Continued)

(58) Field of Classification Search
CPC .. C07C 5/03; C07C 7/144; C07C 7/11; C07C 7/12; C07C 11/06; C07C 9/08; C07C 9/06; C07C 11/04; C07C 5/08
(Continued)

(56) References Cited

U.S. PATENT DOCUMENTS 4,623,443 A * 11/1986 Washer .................. C10G 11/18
208/143
6,297,414 B1 * 10/2001 Barchas .................. C07C 7/163
585/259
(Continued)

FOREIGN PATENT DOCUMENTS

JP 59-123539 7/1984
JP H0363431 B2 10/1991
(Continued)

OTHER PUBLICATIONS

English translation of WO 2009110492 A1 (cited in IDS dated Jun. 12, 2014).*
(Continued)

*Primary Examiner* — Brian A McCaig
*Assistant Examiner* — Jason Y Chong
(74) *Attorney, Agent, or Firm* — Harness, Dickey and Pierce, P.L.C.

(57) ABSTRACT

Provided are a method for producing paraffins and an apparatus for producing paraffins, in which each high-purity paraffin can be produced with high efficiency while complicated operations such as distillation are not carried out. An apparatus for producing paraffins includes a separation and recovery unit and a hydrogenation unit. The separation and recovery unit has a separator containing silver ions, and separates impurities from raw material olefins containing olefins as main components and recovers the olefins, by bringing the raw material olefins into contact with the
(Continued)

separator. The hydrogenation unit brings the olefins recovered by the separation and recovery unit into contact with hydrogen in a presence of a catalyst and subjects the recovered olefins to a hydrogenation reaction, thereby obtaining high-purity paraffins.

12 Claims, 2 Drawing Sheets

(51) Int. Cl.
    *C07C 7/144*     (2006.01)
    *C07C 7/11*     (2006.01)
    *C07C 5/08*     (2006.01)

(52) U.S. Cl.
    CPC .......... *C07C 7/144* (2013.01); *C07C 2521/04* (2013.01); *C07C 2523/42* (2013.01); *C07C 2523/44* (2013.01); *C07C 2523/46* (2013.01); *C07C 2523/755* (2013.01)

(58) Field of Classification Search
    USPC .......................................... 585/264; 422/187
    See application file for complete search history.

(56) References Cited

U.S. PATENT DOCUMENTS

| | | | |
|---|---|---|---|
| 6,468,329 | B2 | 10/2002 | Cho et al. |
| 2002/0005118 | A1 | 1/2002 | Cho et al. |
| 2007/0004954 | A1* | 1/2007 | Asaoka ..................... C10L 3/12 585/733 |
| 2007/0012189 | A1 | 1/2007 | Kang et al. |
| 2009/0270665 | A1 | 10/2009 | Magalhaes Mendes et al. |
| 2011/0245575 | A1* | 10/2011 | Nago ...................... C07C 7/005 585/843 |

FOREIGN PATENT DOCUMENTS

| | | |
|---|---|---|
| JP | 2001-321643 | 11/2001 |
| JP | 2002-356448 | 12/2002 |
| JP | 2007-021473 | 2/2007 |
| JP | 2009-179801 | 8/2009 |
| WO | WO-2009/110492 | 9/2009 |
| WO | WO-2010/074019 | 7/2010 |
| WO | WO-2010/119820 | 10/2010 |

OTHER PUBLICATIONS

Japan Patent Office International Search Report dated Nov. 27, 2012.
International Preliminary Report on Patentability dated Aug. 14, 2014 issued in PCT Application No. PCT/JP2012/074561—with English Translation.
Japanese Office Action dated Dec. 8, 2015 issued in Japanese Patent Application No. 2012-022352 with English concise explanation.
Taiwan Office Action dated Nov. 17, 2015 issued in Taiwan Patent Application No. 101136027 with English concise explanation.
Taiwan Office Action dated Mar. 28, 2015 issued in corresponding Taiwanese Patent Application No. 101136027.

* cited by examiner

METHOD FOR PRODUCING PARAFFINS

TECHNICAL FIELD

The present invention relates to a method for producing paraffins such as ethane and propane, and an apparatus for producing paraffins.

BACKGROUND ART

Propylene, which is one example of lower olefins, has been known as a raw material for synthetic resin products such as polypropylene and acrylonitrile products, or for synthetic rubber products, but in recent years, its uses in the field of semiconductor electronic materials have been widespread. For these uses, propylene is required to have higher purity.

A raw material gas containing propylene as a main component, which is used as a raw material for attaining high purity, includes, for example, methane, ethane, propane, isobutane, and normal butane as impurities. As a method for purifying a propylene gas from the raw material gas, for example, various methods such as membrane separation, adsorption separation, and absorption separation have been known. Among these, methods of membrane separation, adsorption separation, and absorption separation, each using the adsorption characteristics of olefins to the silver ions, have been known.

In Patent Literature 1, a technique for separating and purifying olefins according to a method for membrane separation using silver ions is described. According to the technique described in Patent Literature 1, olefins are separated and purified from raw materials for olefins, containing paraffins as impurities, by using a separation membrane doped with silver ions.

In Patent Literature 2, a technique for separating and purifying olefins according to a method for adsorption separation using silver ions is described. According to the technique described in Patent Literature 2, olefins are separated and purified from raw materials for olefins, containing paraffins as impurities, by using an adsorbent having silver ions carried on alumina.

In Patent Literature 3, a technique for separating and purifying olefins according to a method for absorption separation using silver ions is described. According to the technique described in Patent Literature 3, olefins are separated and purified from raw materials for olefins, containing paraffins as impurities, by using an absorbing liquid containing silver ions.

Furthermore, it could also be found that main impurities included in olefins, which are separated and purified using silver ions, are paraffins and impurities remaining in high-purity olefins obtained by increasing the purity of the olefins are also paraffins. For example, the main impurities in propylene purified by the method described in Patent Literature 3 are propane (about 100 ppm by mole), and thus, high-purity propylene at about 99.99% by mole is obtained.

Meanwhile, propane which is one example of lower paraffins is used in the field of semiconductor electronic materials, for example, in the applications as raw materials for SiC, which is a next-generation power apparatus material, and is used as a propane gas diluted with hydrogen and as a pure gas of propane. For these uses, propane is required to have high purity.

A raw material gas containing propane as a main component, which is used as a raw material for high-purity propane, includes, for example, ethane, propylene, isobutane, and normal butane at high concentrations as impurities.

Examples of a method for purifying propane from the raw material gas include methods of distillation, and membrane separation, adsorption separation, and absorption separation as described above for the purification of olefins. For example, in Patent Literature 4, separation of propylene and propane by a distillation process is described.

CITATION LIST

Patent Literature

Patent Literature 1: Japanese Unexamined Patent Publication JP-A 2001-321643
Patent Literature 2: U.S. Pat. No. 6,468,329 B2
Patent Literature 3: WO2009/110492
Patent Literature 4: Japanese Unexamined Patent Publication JP-A 2002-356448

SUMMARY OF INVENTION

Technical Problem

For example, in the case where propylene and propane are separated by a distillation process as in the technique described in Patent Literature 4, the boiling points thereof are close to each other (a difference in boiling points of 4.9° C.), and it is therefore necessary to repeat distillation in multiple steps for the separation. Accordingly, large-scale facilities and setting of precise distillation conditions are required for their practical uses. The same problems are caused in the case where olefins and paraffins having the same number of carbon atoms are separated from each other by a distillation process.

In addition, the methods by membrane separation, adsorption separation, and absorption separation using silver ions as in the techniques described in Patent Literatures 1 to 3 are excellent as a method for separating and purifying olefins from a raw material gas including olefins, paraffins, and other impurities. However, in the methods by membrane separation, adsorption separation, and absorption separation using silver ions, in the case where paraffins are separated and purified from a raw material gas, impurities other than the olefins easily remain in the paraffins separated from the raw material gas, and therefore, there are many problems in the purification of paraffins with high purity. For example, in the case where propane is purified by separation using silver ions from a raw material gas including methane, ethane, propane, propylene, isobutane, and normal butane, propylene can be separated and removed, but there is a problem that methane, ethane, isobutane, and normal butane remain.

Therefore, an object of the invention is to provide a method for producing paraffins and an apparatus for producing paraffins, in which each high-purity paraffin can be produced with high efficiency while complicated operations such as distillation are not carried out.

Solution to Problem

The present inventors have noted that a small amount of the main impurities included in high-purity olefins, which are separated from paraffins by being brought into contact with silver ions, are paraffins which are targets to be acquired. Further, the present inventors have found that it is unnecessary to remove paraffins as impurities for purification by subjecting the high-purity olefins to a hydrogenation reaction, thereby obtaining high-purity paraffins in a high yield, and thus, completing the invention.

The invention provides a method for producing paraffins including:

a separation and recovery step of separating impurities from raw material olefins containing olefins as main components and recovering the olefins, by bringing the raw material olefins into contact with a separator containing silver ions; and a hydrogenation step of bringing the olefins recovered in the separation and recovery step into contact with hydrogen in a presence of a catalyst and subjecting the recovered olefins to a hydrogenation reaction, thereby obtaining paraffins.

Moreover, in the method for producing paraffins of the invention, it is preferable that the separator is selected from a separation membrane doped with silver ions, an adsorbent having silver ions carried thereon, and an absorbing liquid containing silver ions.

Furthermore, in the method for producing paraffins of the invention, it is preferable that the absorbing liquid is an aqueous silver nitrate solution.

Furthermore, in the method for producing paraffins of the invention, it is preferable that the catalyst is a catalyst containing at least one selected from palladium, rhodium, platinum, ruthenium, and nickel.

Furthermore, in the method for producing paraffins of the invention, it is preferable that the olefins contained in the raw material olefins are olefins having 2 or 3 carbon atoms.

Furthermore, it is preferable that the method for producing paraffins of the invention further includes a pre-hydrogenation step as a step prior to the separation and recovery step, of making acetylene contained in raw material olefins into ethylene by bringing the raw material olefins into contact with hydrogen in a presence of a catalyst and subjecting the raw material olefins to a hydrogenation reaction.

In addition, the invention provides an apparatus for producing paraffins, including:

a separation and recovery unit having a separator containing silver ions, which separates impurities from raw material olefins containing olefins as main components and recovers the olefins, by bringing the raw material olefins into contact with the separator, and a hydrogenation unit which brings the olefins recovered by the separation and recovery unit into contact with hydrogen in a presence of a catalyst and subjects the recovered olefins to a hydrogenation reaction, thereby obtaining paraffins.

Advantageous Effects of Invention

According to the invention, a method for producing paraffins includes a separation and recovery step and a hydrogenation step. In the separation and recovery step, raw material olefins containing paraffins as impurities are brought into contact with a separator containing silver ions. The olefins, which are main components of the raw material olefins, are brought into contact with the silver ions included in the separator to form a complex. Thus, the paraffins that do not form a complex can be separated from the raw material olefins, and thus, olefins can be recovered as a high-purity product. In the hydrogenation step, the high-purity olefins obtained in the separation and recovery step are brought into contact with hydrogen in the presence of a catalyst and subjected to a hydrogenation reaction. Thus, by subjecting the high-purity olefins to a hydrogenation reaction, high-purity paraffins can be obtained.

Moreover, according to the invention, the separator used in the separation and recovery step is selected from a separation membrane doped with silver ions, an adsorbent having silver ions carried thereon, and an absorbing liquid containing silver ions. By using such a separator, olefins can be efficiently separated and recovered from the raw material olefins.

Furthermore, according to the invention, an absorbing liquid as the separator is an aqueous silver nitrate solution. The olefins, which are main components of the raw material olefins in contact with the aqueous silver nitrate solution efficiently, form a complex with silver ions. Thus, olefins, which are main components of the raw material olefins, have an increased difference in the solubility in the aqueous silver nitrate solution from that of other content such as paraffins, and therefore, olefins forming a complex having a high solubility in the aqueous silver nitrate solution can be separated and recovered more effectively. Accordingly, high-purity olefins can be obtained in the separation and recovery step, and thus, high-purity paraffins can be obtained in the hydrogenation step.

In addition, according to the invention, the catalyst used for the hydrogenation reaction of the olefins in the hydrogenation step is a catalyst containing at least one selected from palladium, rhodium, platinum, ruthenium, and nickel. By carrying out the hydrogenation reaction of the olefins in the presence of such a catalyst, the efficiency of the hydrogenation reaction can be improved and the productivity of the high-purity paraffins can be improved.

Moreover, according to the invention, the olefins, which are main components of the raw material olefins, are olefins having 2 or 3 carbon atoms, that is, ethylene and propylene. By subjecting such ethylene and propylene to a hydrogenation reaction in the hydrogenation step, ethane and propane can be produced as the paraffins.

Furthermore, according to the invention, the method for producing paraffins further includes a pre-hydrogenation step as a step prior to the separation and recovery step. In this pre-hydrogenation step, acetylene contained in the raw material olefins is modified to ethylene, which is an olefin, by bringing the raw material olefins into contact with hydrogen in the presence of a catalyst and subjected to a hydrogenation reaction. Thus, high-purity olefins can be obtained in the separation and recovery step by modifying the acetylene contained in the raw material olefins into an olefin in advance prior to the separation and recovery step.

Moreover, according to the invention, the apparatus for producing paraffins includes a separation and recovery unit and a hydrogenation unit. The separation and recovery unit has a separator containing silver ions. The olefins, which are main components of the raw material olefins, form a complex by being brought into contact with silver ions contained in the separator, and thus, paraffins that do not form a complex can be separated from the raw material olefins, whereby it is possible to recover olefins with high purity. In the hydrogenation unit, the high-purity olefins recovered by the separation and recovery unit are brought into contact with hydrogen in the presence of a catalyst and subjected to a hydrogenation reaction. Thus, high-purity paraffins can be obtained by subjecting the high-purity olefins to a hydrogenation reaction.

BRIEF DESCRIPTION OF DRAWINGS

Other and further objects, features, and advantages of the invention will be more explicit from the following detailed description taken with reference to the drawings wherein.

DESCRIPTION OF EMBODIMENTS

Hereinafter, suitable embodiments of the invention will be described in detail with reference to the drawings.

Figure 1:
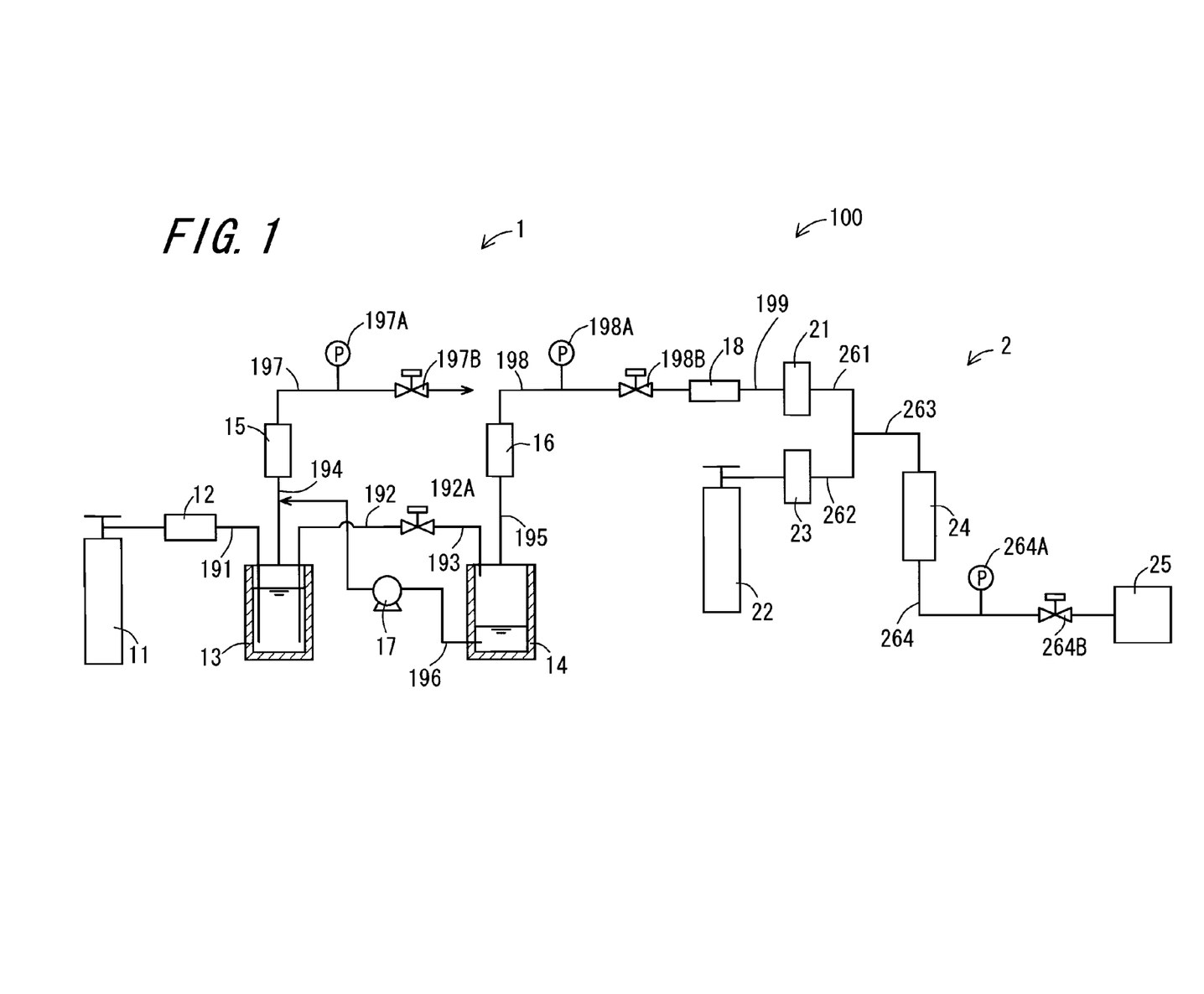
FIG. 1 is a view showing the configuration of an apparatus 100 for producing paraffins according to a first embodiment of the invention.

FIG. 1 is a view showing the configuration of an apparatus 100 for producing paraffins according to a first embodiment of the invention. The apparatus 100 for producing paraffins includes a separation and recovery unit 1 and a hydrogenation unit 2. Further, the method for producing paraffins according to the invention is achieved with the apparatus 100 for producing paraffins, in which the separation and recovery step is carried out with the separation and recovery unit 1 and the hydrogenation step is carried out with the hydrogenation unit 2.

The separation and recovery unit 1 separates impurities from raw material olefins containing olefins as main components (hereinafter referred to as a "raw material gas") and recovers the olefins, by bringing the raw material gas into contact with a separator containing silver ions. Examples of the separator include a separation membrane doped with silver ions, an adsorbent having silver ions carried thereon, and an absorbing liquid containing silver ions. Hereinafter, a case where an absorbing liquid containing silver ions is used as a separator will be described as an example.

The separation and recovery unit 1 includes a raw material cylinder 11, an absorption column 13, a stripping column 14, a first mist remover 15, a second mist remover 16, and a dehydration column 18.

The raw material cylinder 11 is a cylinder charged with a raw material gas containing olefins as main component, and is encapsulated with a raw material gas under a high pressure condition.

Examples of the olefins which are main components of the raw material gas include ethylene, propylene, cyclopropene, 1-butene, 2-butene, isobutene, cyclobutene, 1-methyl cyclopropene, 2-methyl cyclopropene, methylidene cyclopropane, isobutylene, 1,3-butadiene, 1,2-butadiene, cyclopentene, 2-methyl-1-butene, 1-pentene, 2-pentene, 2-methyl-2-butene, 1,4-pentadiene, 1,3-pentadiene, cyclopentene, methylene cyclobutane, vinylcyclopropane, 3-methyl-1,2-butadiene, 1,2-pentadiene, isoprene, 2,3-pentadiene, 1-hexene, 2-hexene, 3-hexene, 4-methyl-2-pentene, 4-methyl-1-pentene, 3,3-dimethyl-1-butene, 2-methyl-pentene, 2,3-dimethyl-1-butene, 2,3-dimethyl-2-butene, 2-methyl-2-pentene, 3-methyl-1-pentene, 3-methyl-2-pentene, 3-methyl-2-pentene, 4-methyl-2-pentene, 2-ethyl-1-butene, 1,5-hexadiene, 1,4-hexadiene, 2,4-hexadiene, 2-methyl-1,3-pentadiene, 2-methyl-1,4-pentadiene, 3-methyl-1,3-pentadiene, 4-methyl-1,3-pentadiene, 2,3-dimethyl-1,3-butadiene, cyclohexene, 1,3-hexadiene, 2,4-hexadiene, 1-methyl-1-cyclopentene, 3-methyl-1,3-pentadiene, 3-methyl-1,4-pentadiene, and methylene cyclopentane.

The invention is effective, particularly for the case of using a raw material gas containing olefins having 2 or 3 carbon atoms (ethylene, propylene, and the like) as main components among the above-described olefins. In the case of using a raw material gas containing olefins having 2 or 3 carbon atoms as main components, paraffins having 2 or 3 carbon atoms are produced by the apparatus 100 for producing paraffins of the present embodiment.

The raw material gas released out of the raw material cylinder 11 is continuously introduced into the absorption column 13. A raw material gas inlet tube 191 provided with a first flow rate controller 12 is connected between the raw material cylinder 11 and the absorption column 13. The raw material gas released out of the raw material cylinder 11 is controlled to a predetermined flow rate by the first flow rate controller 12, flows through the raw material gas inlet tube 191, and is introduced into the absorption column 13. The flow rate of the raw material gas introduced into the absorption column 13 is, for example, from 1 to 100 L/sec per 1 $m^2$ of a cross-sectional area of the column of the absorption column 13, and from 40 to 4000 mL/min in a laboratory scale.

Further, a pre-hydrogenation unit (not shown) may be arranged between the raw material cylinder 11 and the absorption column 13. This pre-hydrogenation unit carries out the pre-hydrogenation step in the method for producing paraffins of the invention. The pre-hydrogenation unit modifies acetylene contained in the raw material gas released out of the raw material cylinder 11 into ethylene which is an olefin by bringing the raw material gas into contact with hydrogen in the presence of a catalyst and subjecting the raw material gas to a hydrogenation reaction. Thus, by modifying the acetylene contained in the raw material gas into an olefin in advance before introducing it to the absorption column 13, high-purity olefins can be obtained by the separation and recovery unit 1. Further, by modifying the acetylene contained in the raw material gas into an olefin in advance, the explosive silver acetylide can be prevented from being stacked in the absorbing liquid containing silver ions stored in the absorption column 13.

Examples of a hydrogenation method, in which acetylene is selectively hydrogenated and thus modified into ethylene but not into ethane by the pre-hydrogenation unit, include a method using a catalyst for selective hydrogenation (Pd/$Al_2O_3$ catalyst) described in Japanese Examined Patent Publication JP-B2 3-63431 (1991).

The absorption column 13 is a sealed container formed in a hollow cylindrical shape, which has an absorbing liquid including a silver ion-containing solution stored in the internal space. This absorbing liquid is, for example, an aqueous silver nitrate solution which is adjusted to a predetermined concentration. One end portion of the raw material gas inlet tube 191 is opened in the absorbing liquid in the lower portion of the absorption column 13. The raw material gas, which is released out of the raw material cylinder 11 and flows through the raw material gas inlet tube 191 toward the absorption column 13, flows into the absorbing liquid from the one end portion of the raw material gas inlet tube 191. In this way, the raw material gas is brought into contact with the absorbing liquid containing silver ions. The raw material gas in contact with the absorbing liquid is absorbed into the absorbing liquid. Since the solubility of the olefins which are main components of the raw material gas in the absorbing liquid is significantly larger than the solubility of the impurities (for example, paraffins) in the raw material gas in the absorbing liquid, the olefins are absorbed preferentially into the absorbing liquid.

As for the absorbing liquid (for example, an aqueous silver nitrate solution) in the absorption column 13, one having a higher concentration causes a larger absorption amount of the olefins per unit volume and unit time, which is thus preferable. From the viewpoint in practical use, in the case where the olefin is propylene, the concentration of the aqueous silver nitrate solution is, for example, in the range of 1 to 6 mol/L, and preferably in the range of 3 to 5 mol/L.

As for the temperature of the aqueous silver nitrate solution, a lower temperature advantageously causes a larger absorption amount of the olefins, and it is, for example, in the range of 0 to 60° C., and more preferably in the range of 0 to 40° C. As for the internal pressure of the absorption column 13, a higher pressure in a constant range causes a larger absorption amount of the olefins, which is thus preferable. From the viewpoint in practical use, the internal pressure of the absorption column 13 is, for example, from 0.1 to 0.8 MPa (gauge pressure; hereinafter referred to as "(G)").

Moreover, a first absorbing liquid outlet tube 192 and a first gas outlet tube 194 are connected to the absorption column 13. The first absorbing liquid outlet tube 192 is a pipe which has one end portion opened in the absorbing liquid in the lower portion of the absorption column 13 and is used to release the absorbing liquid in the absorption column 13 (an absorbing liquid having the raw material gas absorbed therein; hereinafter referred to as a "raw material gas absorbing liquid") out of the column. The other end portion of this first absorbing liquid outlet tube 192 is connected to an absorbing liquid inlet tube 193. The raw material gas absorbing liquid which is released out of the absorption column 13 and flows through the first absorbing liquid outlet tube 192 is adjusted to a predetermined flow rate by a flow rate controlling valve 192A and introduced to the stripping column 14 as described later through the absorbing liquid inlet tube 193.

The first gas outlet tube 194 is a pipe which is connected to the upper portion of the absorption column 13 and is used to release a gas which has not been absorbed into the absorbing liquid stored in the absorption column 13 (unabsorbed gas) out of the column. In this first gas outlet tube 194, one end portion is connected to the upper portion of the absorption column 13 and the other end portion is connected to a first mist remover 15 as described later. The unabsorbed gas which is released out of the absorption column 13 and flows through the first gas outlet tube 194 is introduced into the first mist remover 15.

For the absorption column 13 configured as described above, for example, a known bubble column, a packed column, a wet wall column, a spray column, a scrubber, or a plate column can be employed. Further, the absorption column 13 is equipped with a temperature adjusting device for maintaining the absorbing liquid stored in the absorption column 13 at a desired temperature. In the temperature adjusting device, for example, a temperature-regulating medium composed of a gas or a liquid is allowed to flow though a jacket provided around the absorption column 13.

The raw material gas absorbing liquid released out of the absorption column 13 is introduced into the stripping column 14 through the absorbing liquid inlet tube 193 by a pressure difference between the internal pressure of the absorption column 13 and the internal pressure of the stripping column 14. Further, in the case where the difference in the pressure is small, the raw material gas absorbing liquid may be transported using a pump. The flow rate of the raw material gas absorbing liquid introduced into the stripping column 14 is adjusted by the flow rate controlling valve 192A, and is, for example, from 0.1 to 10 L/sec per 1 m$^2$ of a cross-sectional area of the column of the stripping column 14, and from 5 to 500 mL/min in a laboratory scale.

The stripping column 14 is a sealed container formed in a hollow cylindrical shape, in which a predetermined amount of raw material gas absorbing liquid can be accommodated in the internal space. This stripping column 14 strips the gas components included in the raw material gas absorbing liquid accommodated in the internal space. From the viewpoint of efficiently stripping the gas components, the internal temperature of the stripping column 14 is preferably set to be higher than that of the absorption column 13, and the internal pressure is preferably set to be lower than that of the absorption column 13. The temperature of the raw material gas absorbing liquid in the stripping column 14 is preferably, for example, from 10 to 70° C., and more preferably from 20 to 70° C., in the case where the olefin is propylene. The internal pressure of the stripping column 14 is preferably, for example, −0.09 to 0.3 MPa (G), and more preferably from 0 to 0.3 MPa (G), in the case where the olefin is propylene.

Moreover, a second gas outlet tube 195 and a second absorbing liquid outlet tube 196 are connected to the stripping column 14. The second gas outlet tube 195 is a pipe which is connected to the upper portion of the stripping column 14 and is used to release the gas components stripped from the raw material gas absorbing liquid (hereinafter referred to as a "stripped gas") out of the column. In this second gas outlet tube 195, one end portion is connected to the upper portion of the stripping column 14 and the other end portion is connected to the second mist remover 16 as described later. The stripped gas which is released out of the stripping column 14 and flows through the second gas outlet tube 195 is introduced into the second mist remover 16.

The second absorbing liquid outlet tube 196 is a pipe which has one end portion opened in the raw material gas absorbing liquid in the lower portion of the stripping column 14 and is used to release the raw material gas absorbing liquid in the stripping column 14 (an absorbing liquid having the gas components stripped therein; hereinafter referred to as a "gas component stripping-absorbing liquid") out of the column. In this second absorbing liquid outlet tube 196, the other end portion is connected to an intermediate portion of the first gas outlet tube 194 of the absorption column 13 through a pump 17. The gas component stripping-absorbing liquid which is released out of the stripping column 14 and flows through the second absorbing liquid outlet tube 196 is transported by the pump 17 and returned to the inside of the absorption column 13 through the first gas outlet tube 194.

The stripping column 14 configured as described above is suitably configured to allow the raw material gas absorbing liquid to be liquid-dispersed, and known packed columns, spray columns, or the like, for example, can be employed. Further, the stripping column 14 is equipped with a temperature adjusting device for maintaining the raw material gas absorbing liquid accommodated in the stripping column 14 at a desired temperature.

The unabsorbed gas which is released out of the absorption column 13 and flows through the first gas outlet tube 194 is introduced into the first mist remover 15. The first mist remover 15 separates a mist included in the unabsorbed gas released out of the absorption column 13. A gas discharge tube 197 for directing the gas which has passed through the first mist remover 15 out of the device is connected to the first mist remover 15. A first pressure gauge 197A and a first back-pressure valve 197B are provided in the gas discharge tube 197. In the first back-pressure valve 197B, the opening degree is controlled to adjust the inside of the absorption column 13 to a predetermined pressure.

A stripped gas which is released out of the stripping column 14 and flows through the second gas outlet tube 195 is introduced into the second mist remover 16. Since the stripped gas introduced into the second mist remover 16 is stripped from the raw material gas absorbing liquid, into which the olefins in the raw material gas are preferentially absorbed, in the absorption column 13, the olefin concentration becomes higher than that of the raw material gas. The second mist remover 16 separates a mist included in the stripped gas released out of the stripping column 14. A third gas outlet tube 198 for directing the gas which has passed through the second mist remover 16 to the dehydration column 18 is connected to the second mist remover 16. A second pressure gauge 198A and a second back-pressure valve 198B are provided in the third gas outlet tube 198. In the second back-pressure valve 198B, the opening degree is controlled to adjust the inside of the stripping column 14 to a predetermined pressure.

The dehydration column 18 removes the moisture included in a gas released out of the second mist remover 16 and formed by removing the mist from the stripped gas (a gas having a higher olefin concentration which is higher than that of the raw material gas; hereinafter referred to as a "high-concentration olefin gas"). The dehydration column 18 is charged with an adsorbent for adsorbing the moisture. Examples of such an adsorbent include silica gel, alumina, and zeolite, and examples of the zeolite include Molecular Sieve 3A, Molecular Sieve 4A, and Molecular Sieve 13X. The high-concentration olefin gas formed by removing the moisture by adsorption in the dehydration column 18 is fed into a hydrogenation unit 2 as described later, the concentration of the impurities included in the raw material gas is decreased, and the olefins become high-purity olefins having a higher concentration. Such high-purity olefins are introduced into the hydrogenation unit 2 through a purified olefin outlet tube 199 connected to the dehydration column 18.

According to the separation and recovery unit 1 including the raw material cylinder 11, the absorption column 13, the stripping column 14, the first mist remover 15, the second mist remover 16, and the dehydration column 18 as described above, when the raw material gas is introduced through the raw material gas inlet tube 191 from the raw material cylinder 11 in the absorption column 13, the raw material gas is brought into contact with the absorbing liquid and sequentially absorbed into the absorbing liquid. Since the solubility of the olefins in the absorbing liquid is significantly higher than that of the impurities in the raw material gas, the olefins, which are main components of the raw material gas, are preferentially absorbed into the absorbing liquid. Thus, as the raw material gas goes up while being absorbed into the absorbing liquid, the olefin concentration in the gas decreases, whereas the impurities concentration increases.

On the other hand, for the absorbing liquid in the absorption column 13, while the absorbing liquid which has absorbed the raw material gas in the absorption column 13 (the raw material gas absorbing liquid) is flown out of the absorption column 13 at a predetermined flow rate through the first absorbing liquid outlet tube 192 from the lower portion of the absorption column 13, the absorbing liquid which has stripped the gas components in the stripping column 14 (the gas component stripping-absorbing liquid) is transported by the pump 17 and returned to the absorption column 13 from the upper portion of the absorption column 13 through the first gas outlet tube 194, thereby generating a downward flow in the absorbing liquid in the absorption column 13.

Accordingly, the raw material gas introduced from the raw material gas inlet tube 191 to the absorption column 13 is brought into countercurrent contact with the absorbing liquid flowing downwards in the absorption column 13, and an unabsorbed gas which is not absorbed into the absorbing liquid by such a contact is released to the upper space of the absorption column 13. The unabsorbed gas is delivered to the first mist remover 15 through the first gas outlet tube 194 to separate and remove the liquid components, and then discharged as an off-gas out of the system through the gas discharge tube 197. On the other hand, the liquid components separated by the first mist remover 15 become liquid droplets, drop through the first gas outlet tube 194, and are returned to the absorption column 13.

Thus, in this way, by bringing the raw material gas continuously fed into contact with the absorbing liquid in the absorption column 13, the olefins in the raw material gas are preferentially absorbed into the absorbing liquid, whereas the unabsorbed gas is discharged out of the column.

In the stripping column 14, the gas components in the raw material gas absorbing liquid released out of the absorption column 13 are stripped. The stripped gas stripped from the raw material gas absorbing liquid is delivered to the second mist remover 16 through the second gas outlet tube 195 to remove the liquid components, and then delivered to the dehydration column 18 through the third gas outlet tube 198 to adsorb and remove the moisture, whereby the stripped gas is fed to the hydrogenation unit 2 as the high-purity olefins.

In the stripping column 14, the absorbing liquid in which the gas components are stripped is conveyed to the first gas outlet tube 194 by the pump 17 through the second absorbing liquid outlet tube 196, and thereafter, drops into the absorption column 13. At this time, the flow rate of the absorbing liquid conveyed by the pump 17 is set to the same degree as the flow rate of the absorbing liquid flowing from the absorption column 13 to the stripping column 14. Thus, the absorbing liquid in the absorption column 13 and the absorbing liquid in the stripping column 14 circulate in balance with each other.

In this way, in the stripping column 14, the gas components of the absorbing liquid which continuously flows at a predetermined flow rate are stripped, and at the same time, the stripped gas is released out of the column and fed to the hydrogenation unit 2 as the high-purity olefins through the dehydration column 18.

The hydrogenation unit 2 is means for bringing the high-purity olefins released out of the separation and recovery unit 1 into contact with hydrogen in the presence of a catalyst and subjecting the olefins to a hydrogenation reaction, thereby obtaining high-purity paraffins. The hydrogenation unit 2 includes a hydrogen cylinder 22, a hydrogenation reactor 24, and a recovery container 25.

The high-purity olefins which are released out of the dehydration column 18 of the separation and recovery unit 1 and flow through the purified olefin outlet tube 199 are adjusted to a predetermined flow rate by a second flow rate controller 21, flow through a purified olefin feeding tube 261, and are continuously introduced to a hydrogenation reactor 24 as described later through a mixing pipe 263. The space velocity SV of the high-purity olefins introduced into the hydrogenation reactor 24 is preferably adjusted to 10 to 10000/h, and particularly preferably 200 to 10000/h.

The hydrogen cylinder 22 is a cylinder charged with a hydrogen gas, and is encapsulated with the hydrogen gas under a high pressure condition. The purity of the hydrogen gas is from 99 to 99.99999 mol %, and preferably 99.99999 mol %. If the purity of the hydrogen gas used for the hydrogenation reaction of the high-purity olefins is low, the concentration of the other impurities increases in a mixed gas of the obtained paraffins and hydrogen. The hydrogen gas released out of the hydrogen cylinder 22 is adjusted to a predetermined flow rate by a third flow rate controller 23, flows through a hydrogen feeding tube 262, and is continuously introduced into the hydrogenation reactor 24 through a mixing pipe 263. The flow rate of the hydrogen gas introduced into the hydrogenation reactor 24 is adjusted to a space velocity SV of preferably 10 to 10000/h, and particularly preferably 200 to 10000/h.

The high-purity olefins which flow through the purified olefin feeding tube 261 and the hydrogen gas which flows through the hydrogen feeding tube 262 are mixed in the mixing pipe 263, and introduced into the hydrogenation reactor 24.

The hydrogenation reactor 24 is a sealed container formed in a hollow cylindrical shape, which has a catalyst charged in the internal space. Further, the hydrogenation reactor 24 is equipped with a temperature adjusting device for maintaining the inside of the hydrogenation reactor 24 at a desired temperature. In the hydrogenation reactor 24, the high-purity olefins purified by the separation and recovery unit 1 are brought into contact with the hydrogen gas in the presence of a catalyst and subjected to a hydrogenation reaction, thereby producing high-purity paraffins.

For example, in the case where the raw material gas released out of the raw material cylinder 11 is a gas containing propylene as a main component, the raw material gas includes oxygen, nitrogen, carbon dioxide, carbon monooxide, methane, ethane, propane, ethylene, acetylene, isobutane, normal butane, 1,3-butadiene, and the like as the impurities. In the case where such a raw material gas containing propylene as a main component (hereinafter referred to as "crude propylene") is directly introduced into the hydrogenation unit 2 while not being purified in the separation and recovery unit 1, and subjected to a hydrogenation reaction, thereby producing propane which is a hydrogenation product of propylene, there is a possibility that side reactions such as a shift reaction of the following formula (1) derived from the impurities included in crude propylene, an oxidation reaction of the following formula (2), and hydrogenation reactions of the following formulae (3) and (4) may occur.

[Chem. 1]

$$CO_2 + H_2 \rightarrow H_2O + CO \quad (1)$$

[Chem. 2]

$$C_3H_8 + 5O_2 \rightarrow 3CO_2 + 4H_2O \quad (2)$$

[Chem. 3]

$$C_2H_4 + H_2 \rightarrow C_2H_6 \quad (3)$$

[Chem. 4]

$$CH_2CHCHCH_2 + 2H_2 \rightarrow CH_3CH_2CH_2CH_3 \quad (4)$$

In the case where the shift reaction of the formula (1) occurs, the amount of the impurities other than propane ($C_3H_8$) which is a desired product increases. In the case where the oxidation reaction of the formula (2) occurs, the yield of propane ($C_3H_8$) which is a desired product decreases or the other impurities increase. In the case where the hydrogenation reactions of the formulae (3) and (4) occur, paraffins as the impurities other than propane ($C_3H_8$) which is a desired product increase.

That is, in the case where the raw material gas released out of the raw material cylinder 11 is directly introduced into the hydrogenation unit 2, while not being purified in the separation and recovery unit 1, and subjected to a hydrogenation reaction, high-purity paraffins cannot be produced due to an effect of a side reaction derived from the impurities included in the raw material gas.

On the other hand, in the apparatus 100 for producing paraffins of the present embodiment, the high-purity olefins purified by the separation and recovery unit 1 are subjected to a hydrogenation reaction in the hydrogenation reactor 24. The concentration of the impurities of the high-purity olefins purified by the separation and recovery unit 1 (in the case where the olefin is propylene) is, for example, 1 ppm by mole or less of oxygen, 5 ppm by mole or less of nitrogen, 1 ppm by mole or less of carbon dioxide, and 100 ppm by mole or less of propane.

In the present embodiment, since the high-purity olefins having a very low concentration of the impurities as described above are subjected to a hydrogenation reaction in the hydrogenation reactor 24, the effect of a side reaction derived from the impurities can be inhibited, and thus, high-purity paraffins can be produced.

The catalyst which is charged into the hydrogenation reactor 24 is not particularly limited as long as it is a reduction catalyst, but it is preferably a catalyst containing at least one selected from palladium (Pd), rhodium (Rh), platinum (Pt), ruthenium (Ru), and nickel (Ni), and particularly preferably a catalyst containing palladium (Pd). By carrying out the hydrogenation reaction of the high-purity olefins in the presence of a catalyst, the efficiency of the hydrogenation reaction can be improved and the productivity of the high-purity paraffins can be improved.

Furthermore, the catalyst may be charged into the hydrogenation reactor 24 in the state of being mixed with alumina balls, ceramic balls, or the like. Thus, heat generation due to the hydrogenation reaction in the hydrogenation reactor 24 can be inhibited, and therefore, the reaction temperature can be kept constant.

Moreover, in the hydrogenation reactor 24, the space velocity SV of the high-purity olefins and the hydrogen gas is preferably from 10 to 100000/h, and particularly preferably from 200 to 10000/h. In the case where the space velocity SV is too small, the amount of the catalyst used increases, and thus the cost becomes high. In the case where the space velocity SV is too high, there is a possibility that hydrogenation sufficient for modifying an olefin into a paraffin may not be carried out.

Incidentally, in the hydrogenation reactor 24, the molar ratio of the high-purity olefins to the hydrogen gas is preferably from 1/1 to 1/100, and particularly preferably from 1/1.1 to 1/10 in terms of high-purity olefins/hydrogen. In the case where the molar ratio of hydrogen to high-purity olefins is too low, there is a possibility that hydrogenation sufficient for modifying an olefin into a paraffin may not be carried out. In the case where the molar ratio of hydrogen to the high-purity olefins is too high, too much unreacted hydrogen gas remains in the resulting paraffins.

Furthermore, the temperature in the hydrogenation reactor 24 is preferably from 0 to 700° C., and particularly preferably from 50 to 200° C. In the case where the temperature is too low, a hydrogenation reaction using a catalyst hardly proceeds. Further, in the case where the temperature is too high, cost for facilities for keeping the temperature during the hydrogenation reaction is required, and there is also a possibility that the olefins may be degraded.

In addition, the pressure in the hydrogenation reactor 24 is preferably from 0.0 to 2.0 MPa (G), and particularly preferably from 0.0 to 0.5 MPa (G). The hydrogenation reaction generally tends to be promoted under the condition of a high pressure, but in the case where the pressure is too high, too much reaction heat is generated, which becomes an obstacle for stabilization of the reaction temperature. Further, in the case where the pressure is too high, there is a problem that facilities such as a high pressure compressor are required, and thus, the cost is increased.

In the hydrogenation reactor 24 of the present embodiment, high purity paraffins can be produced by bringing the high-purity olefins purified by the separation and recovery unit 1 into contact with a hydrogen gas in the presence of a catalyst and subjecting the olefins to a hydrogenation reaction.

The high purity paraffins produced by the hydrogenation reaction of the high-purity olefins in the hydrogenation reactor 24 are conveyed to a recovery container 25 through a purified paraffin outlet tube 264 together with the hydrogen gas, and accommodated in the recovery container 25. The high purity paraffins accommodated in the recovery container 25 is a mixture with hydrogen. Further, a third pressure gauge 264A and a third back-pressure valve 264B are provided in the purified paraffin outlet tube 264. The opening degree of the third back-pressure valve 264B is controlled such that the inside of the hydrogenation reactor 24 is adjusted to a predetermined pressure.

Accordingly, by bringing the high-purity olefins purified by the separation and recovery unit 1 into contact with the hydrogen gas in the presence of a catalyst by the hydrogenation unit 2 and subjecting the olefins to a hydrogenation reaction in the apparatus 100 for producing paraffins of the present embodiment, high-purity paraffins can be efficiently obtained while not carrying out complicated operations such as distillation.

Figure 2:
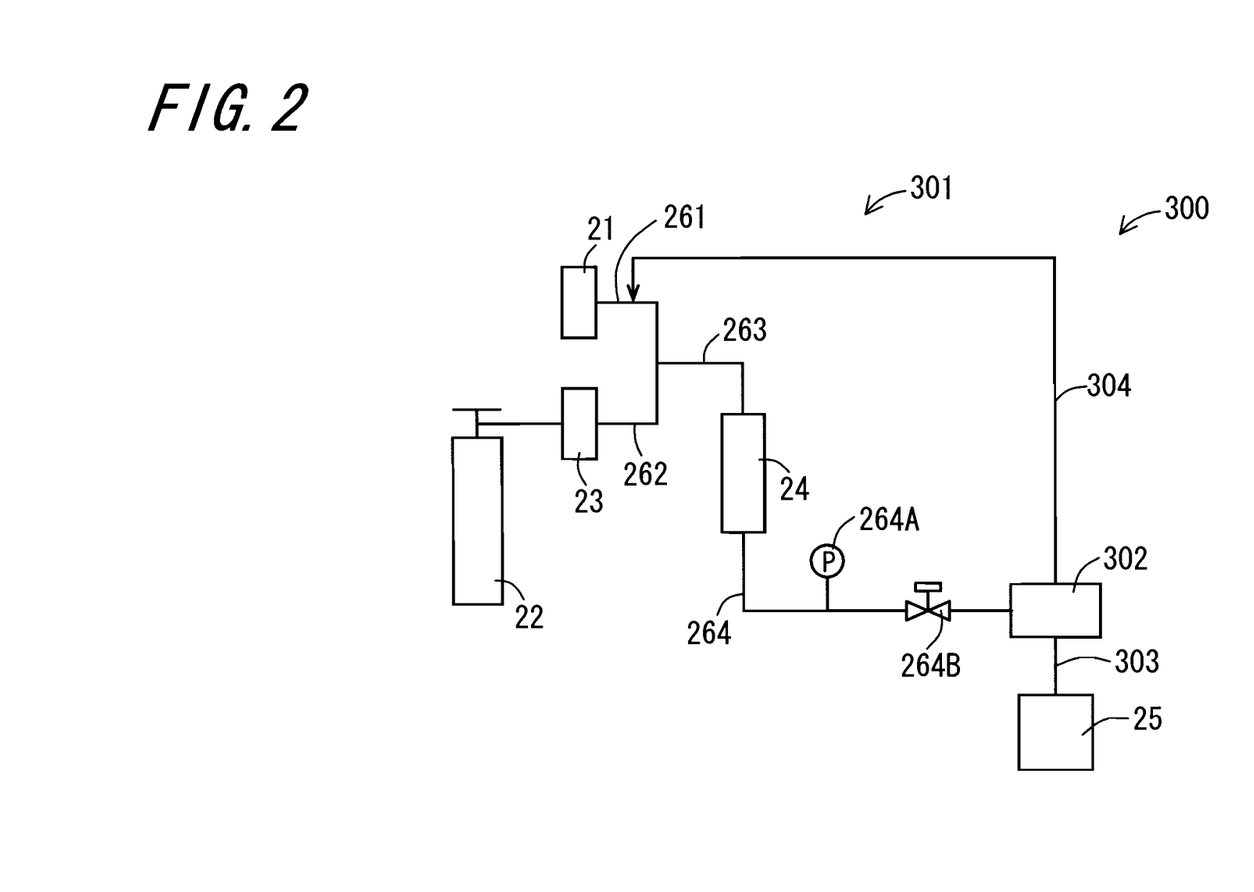
FIG. 2 is a view showing the configuration of an apparatus 300 for producing paraffins according to a second embodiment of the invention.

FIG. 2 is a view showing the configuration of an apparatus 300 for producing paraffins according to a second embodiment of the invention. The apparatus 300 for producing paraffins of the present embodiment is similar to the above-described apparatus 100 for producing paraffins, and the description thereof is omitted using the same reference numerals for the corresponding parts. In the apparatus 300 for producing paraffins, the configuration of the hydrogenation unit 301 is different from that of the hydrogenation unit 2 of the above-described apparatus 100 for producing paraffins. This apparatus 300 for producing paraffins includes the separation and recovery unit 1 in the same manner as for the apparatus 100 for producing paraffins, but the separation and recovery unit 1 is omitted in FIG. 2.

The hydrogenation unit 301 of the apparatus 300 for producing paraffins is the same as the hydrogenation unit 2 of the apparatus 100 for producing paraffins except that it further includes a hydrogen separation apparatus 302.

The hydrogen separation apparatus 302 is an apparatus for separating and removing the hydrogen from a mixture of the high purity paraffins and hydrogen, released out of the hydrogenation reactor 24. Further, the hydrogen separation apparatus 302 can remove a low-boiling point gas such as nitrogen and oxygen gases, in addition to hydrogen. Examples of such a hydrogen separation apparatus 302 include a condenser for separating and removing hydrogen from a mixture by partial condensation of the mixture, and a hydrogen separating membrane apparatus for separating and removing hydrogen from a mixture using a hydrogen separating membrane.

The high-purity paraffins formed by separating and removing hydrogen by the hydrogen separation apparatus 302 are conveyed from the lower portion of the hydrogen separation apparatus 302 to a recovery container 25 through a purified paraffin outlet tube 303, and accommodated in the recovery container 25.

Furthermore, a hydrogen outlet tube 304 is connected to the hydrogen separation apparatus 302. The hydrogen outlet tube 304 is a pipe which is connected to the upper portion of the hydrogen separation apparatus 302 and is used to release the hydrogen gas separated from a mixture of high-purity paraffins and hydrogen out of the apparatus. In the hydrogen outlet tube 304, one end portion is connected to the upper portion of the hydrogen separation apparatus 302 and the other end portion is connected to an intermediate portion of the purified olefin feeding tube 261 for introducing the high-purity olefins into the hydrogenation reactor 24.

The hydrogen which is released out of the hydrogen separation apparatus 302 and flows through the hydrogen outlet tube 304 is returned to the inside of the hydrogenation reactor 24 through the purified olefin feeding tube 261, and can thus be used as a hydrogen source for a hydrogenation reaction in the hydrogenation reactor 24. The hydrogen gas separated from the mixture may not also be returned to the inside of the hydrogenation reactor 24, but may be discharged from the system.

EXAMPLES

Hereinafter, the invention will be described in more detail with reference to Examples, but the invention is not limited to the Examples.

Example 1

<Production of High-Purity Olefins>

As a raw material gas, crude propylene (a propylene concentration of 99.5 mol %, and a propane concentration of 0.5 mol %, manufactured by Mitsui Chemicals, Inc.) containing propylene as a main component was used. This crude propylene was fed to the separation and recovery unit 1 shown in FIG. 1, using an aqueous silver nitrate solution as an absorbing liquid at a flow rate of 663 mL/min, and purified. Specifically, as each of an absorption column 13 and a stripping column 14, including a bubble column, a cylindrical tube made of stainless steel (an inner diameter of 54.9 mm×a height of 500 mm, a volume of 1185 mL) was used. In the absorption column 13, 5 mol/L of the aqueous silver nitrate solution was stored in the amount of 735 mL (a height of the liquid surface of the absorbing liquid of 310 mm), and in the stripping column 14, an aqueous silver nitrate solution having the same concentration was stored in the amount of 355 mL (a height of the liquid surface of the absorbing liquid of 150 mm).

As a condition in the absorption column 13, the internal pressure was set to 0.5 MPa (G) and the internal temperature was set to 25° C. As a condition in the stripping column 14, the internal pressure was set to 0.1 MPa (G) and the internal temperature was set to 25° C. The aqueous silver nitrate solution stored in the absorption column 13 and the stripping column 14 was circulated at a flow rate of 25 mL/min. In the stripping column 14, the stripped gas (purified propylene gas) was released out at 637 mL/min and the recovery rate was 96.1 mol %. Further, in the absorption column 13, the unabsorbed gas was discharged at 26 mL/min and the discharge rate was 3.9 mol %.

The purity of the propylene gas obtained by the separation and recovery unit 1 was analyzed by gas chromatography (FID) and it was found that the purity was 99.99 mol % and the impurity concentration in terms of propane which is a main impurity was 56 ppm by mole.

<Production of Paraffins>

The high-purity propylene gas obtained by the separation and recovery unit 1 was fed at a flow rate of 40 mL/min to a hydrogenation reactor 24 of the hydrogenation unit 2 shown in FIG. 1. Further, a hydrogen gas having a purity of 99.9999 mol % was fed at a flow rate of 60 mL/min from the hydrogen cylinder 22 to the hydrogenation reactor 24. As the hydrogenation reactor 24, a cylindrical tube made of stainless steel (an inner diameter of 12.4 mm×a height of 50 mm) was used. The hydrogenation reactor 24 was charged with 6 mL of a Pd (0.5% by weight)/$Al_2O_3$ catalyst (N1182AZ, manufactured by JGC Catalysts and Chemicals Ltd.). As a condition for the hydrogenation reaction in the hydrogenation reactor 24, the internal pressure was set to 0.1 MPa (G) and the internal temperature was set to 150° C.

The resulting gas released out of the hydrogenation reactor 24 was a mixed gas of a propane gas and a hydrogen gas (molar ratio of propane/hydrogen=2/1), and the impurity concentration in terms of propylene which is a main impurity in the resulting gas was analyzed by gas chromatography (FID) and found to be 1 ppm by mole or less.

Thus, in Example 1, high-purity propane having a propylene concentration of 1 ppm by mole or less was obtained, using crude propylene having a propylene concentration of 99.5 mol % and a propane concentration of 0.5 mol % as a raw material.

Example 2

<Production of High-Purity Olefins>

As a raw material gas, crude ethylene having ethylene as a main component (an ethylene concentration of 99.4 mol %, an ethane concentration of 0.6 mol %, manufactured by Nippon Fine Gas Co., Ltd.) was used. This crude ethylene was fed at a flow rate of 800 mL/min to the separation and recovery unit 1 shown in FIG. 1, using an aqueous silver nitrate solution as an absorbing liquid, and purified. In the absorption column 13, 3 mol/L of the aqueous silver nitrate solution was stored in the amount of 237 mL (a height of the liquid surface of the absorbing liquid of 100 mm), and in the stripping column 14, an aqueous silver nitrate solution having the same concentration was stored in the amount of 355 mL (a height of the liquid surface of the absorbing liquid of 150 mm).

As a condition in the absorption column 13, the internal pressure was set to 0.5 MPa (G) and the internal temperature was set to 25° C. As a condition in the stripping column 14, the internal pressure was set to 0.1 MPa (G) and the internal temperature was set to 40° C. The aqueous silver nitrate solution stored in the absorption column 13 and the stripping column 14 was circulated at a flow rate of 25 mL/min. In the stripping column 14, the stripped gas (purified ethylene gas) was released out at 760 mL/min and the recovery rate was 95.0 mol %. Further, in the absorption column 13, the unabsorbed gas was discharged at 40 mL/min and the discharge rate was 5.0 mol %.

The purity of the ethylene gas obtained by the separation and recovery unit 1 was analyzed by gas chromatography (FID) and it was found that the purity was 99.99 mol % and the impurity concentration in terms of ethane which is a main impurity was 33 ppm by mole.

<Production of Paraffins>

The high-purity ethylene gas obtained by the separation and recovery unit 1 was fed at a flow rate of 40 mL/min to the hydrogenation reactor 24 of the hydrogenation unit 2 shown in FIG. 1. Further, a hydrogen gas having a purity of 99.9999 mol % was fed at a flow rate of 60 mL/min from the hydrogen cylinder 22 to the hydrogenation reactor 24. The hydrogenation reactor 24 was charged with 12 mL of an Rh (0.5% by weight)/$Al_2O_3$ catalyst (manufactured by Aldrich Chemical Co., Inc.). As a condition for the hydrogenation reaction in the hydrogenation reactor 24, the internal pressure was set to 0.1 MPa (G) and the internal temperature was set to 130° C.

The resulting gas released out of the hydrogenation reactor 24 was a mixed gas of an ethane gas and a hydrogen gas (molar ratio of ethane/hydrogen=2/1), and the impurity concentration in terms of ethylene which is a main impurity in the resulting gas was analyzed by gas chromatography (FID) and found to be 1 ppm by mole or less.

Thus, in Example 2, high-purity ethane having an ethylene concentration of 1 ppm by mole or less was obtained, using crude ethylene having an ethylene concentration of 99.4 mol % and an ethane concentration of 0.6 mol % as a raw material.

Example 3

<Production of High-Purity Olefins>

As a separator in the separation and recovery unit, a separation membrane doped with silver ions was used. This separation membrane was specifically a sulfonic acid type perfluorinated cation exchange membrane which had been subjected to exchange with silver ions. The sulfonic acid type perfluorinated cation exchange membrane was subjected to exchange with counter ions by immersing the membrane in an aqueous silver nitrate solution at a concentration of 1 mol/L for 24 hours or longer. After eliminating the solution adhered to the surface of the membrane and drying naturally at 25° C. for 24 hours, silver ion-exchanged sulfonic acid type perfluorinated cation membrane was fabricated. Using this silver ion-exchange membrane, membrane separation was carried out. A general apparatus widely known was used as a membrane separation apparatus.

As a raw material gas, crude propylene (a propylene concentration of 99.5 mol %, a propane concentration of 0.5 mol %, manufactured by Mitsui Chemicals, Inc.) containing propylene as a main component was used. The purification of crude propylene by membrane separation was carried out in parallel flow. The crude propylene was allowed to flow continuously at a flow rate of 200 mL/min to the silver ion-exchange membrane and the membrane separation apparatus was driven while keeping the difference in the pressures between the inside and the outside of the membrane at 0.4 MPa.

The impurity concentration in terms of propane which is a main impurity in the propylene gas obtained by the membrane separation apparatus was analyzed by gas chromatography (FID) and found to be 800 ppm by mole. Further, the separation coefficient α of the silver ion-exchange membrane was 5.8.

<Production of Paraffins>

The high-purity propylene gas obtained by the membrane separation apparatus was fed at a flow rate of 40 mL/min to the hydrogenation reactor 24 of the hydrogenation unit 2 shown in FIG. 1. Further, a hydrogen gas having a purity of 99.9999 mol % was fed at a flow rate of 60 mL/min from the hydrogen cylinder 22 to the hydrogenation reactor 24. As the hydrogenation reactor 24, a cylindrical tube made of stainless steel (an inner diameter of 12.4 mm×a height of 50 mm) was used. The hydrogenation reactor 24 was charged with 6 mL of a Pd (0.5% by weight)/$Al_2O_3$ catalyst (N1182AZ, manufactured by JGC Catalysts and Chemicals Ltd.). As a condition for the hydrogenation reaction in the hydrogenation reactor 24, the internal pressure was set to 0.0 MPa (G) and the internal temperature was set to 170° C.

The resulting gas released out of the hydrogenation reactor 24 was a mixed gas of a propane gas and a hydrogen gas (molar ratio of propane/hydrogen=2/1), and the impurity concentration in terms of propylene which is a main impurity in the resulting gas was analyzed by gas chromatography (FID) and found to be 1 ppm by mole or less.

Thus, in Example 3, high-purity propane having a propylene concentration of 1 ppm by mole or less was obtained, using crude propylene having a propylene concentration of 99.5 mol % and a propane concentration of 0.5 mol % as a raw material.

Example 4

<Production of High-Purity Olefins>

As a separator of a separation and recovery unit, an adsorbent having silver ions carried thereon was used. This adsorbent is specifically an adsorbent formed by impregnating Y type zeolite (320 HOA, manufactured by Tosoh Corporation) with silver nitrate at 24% by weight. An apparatus in which this adsorbent was charged into an adsorption column (20 A×300 mm) was used as a separation and recovery unit.

As a raw material gas, crude propylene (a propylene concentration of 99.5 mol %, a propane concentration of 0.5 mol %, manufactured by Mitsui Chemicals, Inc.) containing propylene as a main component was used. The operation of the adsorption separation was carried out as follows. In the adsorption step, the crude propylene was fed to the adsorption column and crushed, and then bubbled at 150 mL/min for 15 minutes. Thereafter, the propylene gas released out of the adsorption column was recovered under reduced pressure (~10 mmHg).

The impurity concentration in terms of propane which is a main impurity in the propylene gas obtained by the operation of the adsorption separation was analyzed by gas chromatography (FID) and found to be 110 ppm by mole.

<Production of Paraffins>

The high-purity propylene gas obtained by the operation of the adsorption separation was fed at a flow rate of 40 mL/min to the hydrogenation reactor 24 of the hydrogenation unit 2 shown in FIG. 1. Further, a hydrogen gas having a purity of 99.9999 mol % was fed at a flow rate of 60 mL/min from the hydrogen cylinder 22 to the hydrogenation reactor 24. As the hydrogenation reactor 24, a cylindrical tube made of stainless steel (an inner diameter of 12.4 mm×a height of 100 mm) was used. The hydrogenation reactor 24 was charged with a mixture of 6 mL of an Rh (0.5% by weight)/$Al_2O_3$ catalyst (manufactured by Aldrich Chemical Co., Inc.) and 6 mL of alumina balls having a diameter of 2 mm (HD-2, manufactured by Sumitomo Chemical Co., Ltd). As a condition for the hydrogenation reaction in the hydrogenation reactor 24, the internal pressure was set to 0.2 MPa (G) and the internal temperature was set to 200° C.

The resulting gas released out of the hydrogenation reactor 24 was a mixed gas of a propane gas and a hydrogen gas (molar ratio of propane/hydrogen=2/1), and the impurity concentration in terms of propylene which is a main impurity in the resulting gas was analyzed by gas chromatography (FID) and found to be 1 ppm by mole or less.

Thus, in Example 4, high-purity propane having a propylene concentration of 1 ppm by mole or less was obtained, using crude propylene having a propylene concentration of 99.5 mol % and a propane concentration of 0.5 mol % as a raw material.

Example 5

<Production of High-Purity Olefins>

An apparatus for producing paraffins, in which a pre-hydrogenation unit was arranged between the raw material cylinder 11 and the separation and recovery unit 1, was used. In the pre-hydrogenation unit, crude ethylene having 5 ppm by mole of acetylene as the impurities (an ethylene concentration of 99.4 mol % and an ethane concentration of 0.6 mol %) was subjected to a selective hydrogenation reaction. As the pre-hydrogenation unit, specifically one having a cylindrical tube made of stainless steel (an inner diameter of 12.4 mm×a height of 50 mm) charged with 6 mL of a Pd (0.5% by weight)/$Al_2O_3$ catalyst (N1182AZ, manufactured by JGC Catalysts and Chemicals Ltd.) was used.

The crude ethylene gas was fed at a flow rate of 40 mL/min to the pre-hydrogenation unit and the hydrogen gas having a purity of 99.9999 mol % was fed thereto at a flow rate of 60 mL/min. As a condition for the hydrogenation reaction in the pre-hydrogenation unit, the internal pressure was set to 0.0 MPa (G) and the internal temperature was set to 100° C. Acetylene was not detected in the resulting gas (ethylene gas) released out of the pre-hydrogenation unit.

The ethylene gas formed by removing acetylene as described above was fed at a flow rate of 800 mL/min to the separation and recovery unit 1 shown in FIG. 1, using an aqueous silver nitrate solution as an absorbing liquid, and purified. 3 mol/L of the aqueous silver nitrate solution was stored in the amount of 237 mL (a height of the liquid surface of the absorbing liquid of 100 mm) in the absorption column 13, and an aqueous silver nitrate solution having the same concentration was stored in the amount of 355 mL (a height of the liquid surface of the absorbing liquid of 150 mm) in the stripping column 14.

As a condition in the absorption column 13, the internal pressure was set to 0.5 MPa (G) and the internal temperature was set to 25° C. As a condition in the stripping column 14, the internal pressure was set to 0.1 MPa (G) and the internal temperature was set to 40° C. The aqueous silver nitrate solution stored in the absorption column 13 and the stripping column 14 was circulated at a flow rate of 25 mL/min. In the stripping column 14, the stripped gas (purified ethylene gas) was released out at 760 mL/min and the recovery rate was 95.0 mol %. Further, in the absorption column 13, the unabsorbed gas was discharged at 40 mL/min and the discharge rate was 5.0 mol %.

The purity of the ethylene gas obtained by the separation and recovery unit 1 was analyzed by gas chromatography (FID) and it was found that the purity was 99.99 mol % and the impurity concentration in terms of ethane which is a main impurity was 33 ppm by mole.

<Production of Paraffins>

The high-purity ethylene gas obtained by the separation and recovery unit 1 was fed at a flow rate of 40 mL/min to the hydrogenation reactor 24 of the hydrogenation unit 2 shown in FIG. 1. Further, a hydrogen gas having a purity of 99.9999 mol % was fed at a flow rate of 60 mL/min from the hydrogen cylinder 22 to the hydrogenation reactor 24. The hydrogenation reactor 24 was charged with 12 mL of an Rh (0.5% by weight)/$Al_2O_3$ catalyst (manufactured by Aldrich Chemical Co., Inc.). As a condition for the hydrogenation reaction in the hydrogenation reactor 24, the internal pressure was set to 0.1 MPa (G) and the internal temperature was set to 130° C.

The resulting gas released out of the hydrogenation reactor 24 was a mixed gas of an ethane gas and a hydrogen gas (molar ratio of ethane/hydrogen=2/1), and the impurity concentration in terms of ethylene which is a main impurity in the resulting gas was analyzed by gas chromatography (FID) and found to be 1 ppm by mole or less.

Thus, in Example 5, high-purity ethane having an ethylene concentration of 1 ppm by mole or less was obtained, using crude ethylene having an ethylene concentration of 99.4 mol % and an ethane concentration of 0.6 mol % as a raw material.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

REFERENCE SIGNS LIST

1: Separation and recovery unit
2, 301: Hydrogenation unit
11: Raw material cylinder
12: First flow rate controller
13: Absorption column
14: Stripping column
15: First mist remover
16: Second mist remover
17: Pump
18: Dehydration column
21: Second flow rate controller
22: Hydrogen cylinder
23: Third flow rate controller
24: Hydrogenation reactor
25: Recovery container
100, 300: Apparatus for producing paraffins
302: Hydrogen separation apparatus

The invention claimed is:

1. A method for producing paraffins, comprising:
    separating impurities from raw material olefins containing olefins as main components and recovering the olefins having a purity of 99.99 mol % or more, by bringing the raw material olefins into contact with a separator containing silver ions; and
    bringing the recovered olefins into contact with hydrogen in a presence of a catalyst and subjecting the recovered olefins to a hydrogenation reaction, thereby recovering paraffins having a purity of 99.99 mol % or more.

2. The method for producing paraffins according to claim 1, wherein the separator is selected from a separation membrane doped with silver ions, an adsorbent having silver ions carried thereon, and an absorbing liquid containing silver ions.

3. The method for producing paraffins according to claim 2, wherein the absorbing liquid is an aqueous silver nitrate solution.

4. The method for producing paraffins according to claim 1, wherein the catalyst is a catalyst containing at least one selected from palladium, rhodium, platinum, ruthenium, and nickel.

5. The method for producing paraffins according to claim 4, wherein the catalyst contains palladium or rhodium.

6. The method for producing paraffins according to claim 5, wherein the catalyst comprises $Al_2O_3$.

7. The method for producing paraffins according to claim 4, wherein the catalyst comprises $Al_2O_3$.

8. The method for producing paraffins according to claim 1, wherein the olefins contained in the raw material olefins are olefins having 2 or 3 carbon atoms.

9. The method for producing paraffins according to claim 1, further comprising, prior to separating impurities from raw material olefins and recovering the olefins, converting acetylene contained in the raw material olefins into ethylene by bringing the raw material olefins into contact with hydrogen in a presence of a catalyst and subjecting the raw material olefins to a hydrogenation reaction.

10. The method for producing paraffins according to claim 9, wherein the raw material olefins contain olefins in a concentration of at least about 99.4 mol %.

11. The method for producing paraffins according to claim 1, wherein the raw material olefins contain olefins in a concentration of at least about 99.4 mol %.

12. The method for producing paraffins according to claim 1, wherein the method is carried out without any distillation steps.

* * * * *